United States Patent [19]

Yokozeki et al.

[11] Patent Number: 4,711,846

[45] Date of Patent: Dec. 8, 1987

[54] PROCESS FOR THE PRODUCTION OF L-ASPARTYL-L-PHENYLALANINE METHYL-ESTER OR L-ASPARTYL-L-PHENYLALANINE

[75] Inventors: Kenzo Yokozeki; Koji Kubota, both of Kawasaki, Japan

[73] Assignee: Ajinomoto Company, Incorporated, Tokyo, Japan

[21] Appl. No.: 604,523

[22] Filed: Apr. 27, 1984

[30] Foreign Application Priority Data

Apr. 28, 1983 [JP] Japan ................................. 58-75558
Apr. 28, 1983 [JP] Japan ................................. 58-75559

[51] Int. Cl.[4] ........................ C12P 21/02; C12R 1/19; A23L 1/236
[52] U.S. Cl. ..................................... 435/70; 426/548; 435/849

[58] Field of Search ................... 435/70, 68, 849, 253; 426/548

[56] References Cited

U.S. PATENT DOCUMENTS 4,284,721 8/1981 Oyama et al. ........................ 435/70
4,506,011 3/1985 Harada et al. ........................ 435/70

Primary Examiner—John E. Tarcza
Attorney, Agent, or Firm—Oblon, Fisher, Spivak, McClelland & Maier

[57] ABSTRACT

A process for the production of L-aspartyl-L-phenylalanine methyl ester of L-aspartyl-L-phenylalanine by contacting an appropriate microorganism or enzyme-containing fraction of said microorganism with L-aspartic acid and L-phenylalanine methyl ester or L-phenylalanine in an aqueous medium so that L-aspartyl-L-phenylalanine methyl ester or L-aspartyl-L-phenylalanine is produced.

4 Claims, No Drawings

4,711,846

PROCESS FOR THE PRODUCTION OF L-ASPARTYL-L-PHENYLALANINE METHYL ESTER OR L-ASPARTYL-L-PHENYLALANINE

BACKGROUND OF THE INVENTION

Field of the Invention

This invention relates to a process for producing L-aspartyl-L-phenylalanine methyl ester (abbreviated as APM hereinafter) or L-aspartyl-L-phenylalanine (abbreviated as AP hereinafter).

Description of the Prior Art

APM is a peptide which is noted as a sweetener in recent years.

It is well-known that the processes for the production of APM or AP include a chemical synthesizing process and an enzymatic synthesizing process.

The chemical synthesizing process for the production of APM comprises condensing N-protected L-aspartic acid anhydride and L-phenylalanine methyl ester (abbreviated as PM hereinafter) to obtain N-protected APM and then removing the protective group afterwards. The enzymatic synthesizing process comprises exerting the effect of a protein-decomposing enzyme on N-protected L-aspartic acid and PM to obtain N-protected APM or the PM adduct of N-protected APM and then removing the protective group to form APM. However, both processes require the complicated steps of introducing the protective groups and removing the same.

There is also known a process for producing APM without using the protective groups (Japanese Patent Kokai No. 43793/1983, "Digests of the Publications at the Annual Meeting of the Agricultural Chemical Society of Japan" in 1983, p. 42) which is a microbiological synthetic process using one of Pseudomonas, Torulopsis, Rhodotorula, and Sporobolomyces, but this is not always suitable for the industrial production of APM because of the extremely low yields.

SUMMARY OF THE INVENTION

The inventors of this application have eagerly sought a more effective process than the conventional one and have found that the employment of microorganisms brings about the direct and effective formation of APM from L-aspartic acid and PM, or AP from L-aspartic acid and L-phenylalanine (abbreviated as P hereinafter).

Accordingly, this invention is directed to a process for the production of APM or AP, characterized by exerting the action of a microorganism chosen from one of the following groups: Corynebacterium, Candida, Cryptococcus, Escherichia, Flavobacterium, Geotrichum, Micrococcus, Pachysolen, Saccharomyces, Trichosporon, Xanthomonas, Kluyveromyces, and Endomyces, and which has the ability to form APM or AP by the condensation of L-aspartic acid and PM or P to produce APM or AP.

The process for converting L-aspartic acid and PM to APM or L-aspartic acid and P to AP by conducting the condensation in an aqueous medium utilizing the action of microorganisms having the abiity to form APM or AP by the condensation of L-aspartic acid and PM or P can easily be carried out only by contacting L-aspartic acid and PM or P with the microorganism cells, culture solutions or microorganism cell-treating materials of the above-mentioned microorganisms.

DETAILED DESCRIPTION OF THE PREFERRED EMBODIMENTS

The following are examples of the microorganisms which have the ability to change L-aspartic acid and PM to APM or L-aspartic acid and P to AP by the condensation in this invention:

| | |
|---|---|
| Corynebacterium sp. | ATCC 21251 |
| Corynebacterium xerosis | ATCC 373 |
| Candida intermedia | FERM-BP 508 |
| Cryptococcus neoformans | IFO 4289 |
| Escherichia coli | FERM-BP 477 |
| Flavobacterium sewanens | FERM-BP 476 |
| Geotrichum candidum | IFO 4599 |
| Micrococcus luteus | ATCC 4698 |
| Pachysolen tannophilus | IFO 1007 |
| Trichosporon capitatum | IFO 1197 |
| Xanthomonas campestris | FERM-BP 507 |
| Kluyveromyces thermotolerans | IFO 0662 |
| Endomyces ovetencis | IFO 1201 |
| Saccharomyces cerevisiae | IFO 2003 |
| Arthrobacter citreus | ATCC 11624 |
| Cellulomonas flavigena | ATCC 8183 |
| Brevibacterium linens | ATCC 8377 |

The cells of these microorganisms can be obtained by using ordinary culture media. Further, L-aspartic acid and PM or P may be added at the beginning or in the process of cultivation.

The culture media to be used for the microorganisms of this invention are ordinary ones containing usual carbon and nitrogen sources and inorganic ions in addition to L-aspartic acid and PM or P. Moreover, the addition of trace amounts of organic nutritive substances such as vitamins and amino acids often brings about desirable results.

The carbon sources suitable for use herein include carbohydrates such as glucose and sucrose, organic acids such as acetic acid, alcohols, and so on. The nitrogen sources suitable for use herein include ammonia gas, aqueous ammonia, ammonium salts, and so on. The inorganic ions are properly selected from magnesium ion, phosphoric ion, potassium ion, iron ion and so on when necessary.

The cultures are conducted under aerobic conditions at pH 4–8, at suitable temperatures controlled within the range of 25°–40° C., and for 1–10 days to obtain desirable results.

The microorganisms to be used in this invention include the whole culture solutions obtained after completion of the cultivation thereof, the microorganisms separated from the culture solutions, or washed microorganisms. Also, the microorganisms to be used in this invention may be freeze-dried, acetone-dried, contacted with toluene, surfactants, etc., treated with lysozyme, exposed to ultrasonic waves, mechanically ground. By microorganism is meant any of the above-mentioned treated or untreated microorganisms.

Furthermore, since it is an enzyme or a combination of enzymes contained in the microorganisms which bring about the condensation of the substrates to form the product, any fraction of the microorganisms which contains said enzyme or enzymes may be used in the practice of this invention. For example, an enzyme protein fraction, insolubilized materials resulting from the above-mentioned treatments, etc. may be used by the method of this invention. By enzyme-containing fraction of a microorganism is meant any such microorganism-derived, enzyme-containing material that is capable of bringing about the stated chemical reactions. One skilled in the art can easily determine whether any unknown microorganism or enzyme-containing fraction is within the scope of this invention by contacting the microorganism or fraction with the named starting materials and monitoring the formation of reaction products as described herein.

As aqueous media, there can be used those containing water, buffers, and organic solvents such as ethanol. Moreover, nutritive elements needed for the growth of microorganisms, anti-oxidants, surfactants, coenzymes, hydroxylamine and metallic ions, etc. can be added to the aqueous media if necessary.

When the cells of the above-mentioned microorganisms are grown in aqueous media and simultaneously brought into contact with L-aspartic acid and PM or P to exert the action thereon, the aqueous media should contain L-aspartic acid, PM or P, and also nutritive elements such as carbon sources, nitrogen sources, and inorganic ions, etc. needed for the growth of the microorganisms. Further, the addition of trace amounts of organic nutritive elements such as vitamins and amino acids often brings about desirable results.

The carbon sources suitable for use herein include carbohydrates such as glucose and sucrose, organic acids such as acetic acid, alcohols, and so on. The nitrogen sources suitable for use herein include ammonia gas, aqueous ammonia, ammonium salts, and so on. The inorganic ions are properly selected from magnesium ion, phosphoric acid ion, potassium ion, iron ion, and so on when necessary.

The microorganisms are grown under aerobic conditions at pH 4-8, and at proper temperatures controlled within the range of 25°-40° C. to obtain desirable results.

Thus, L-aspartic acid and PM or P are efficiently converted to APM or AP only when incubated for 1-10 days.

When the whole culture solutions, culture cells or cell-treating materials of the above-mentioned microorganisms are brought directly into contact with L-aspartic acid and PM or P to exert the action thereon, the aqueous media prepared by dissolving or suspending L-aspartic acid, PM, or P and the culture solutions, microorganism culture cells, or microorganism cell-treating materials, and are controlled at proper temperatures of 10°-70° C., kept at pH 4-8, and allowed to stand for a while or stirred, a great deal of AMP or AP is produced and accumulated in the aqueous media after 5-100 hours.

The APM or AP thus produced can be separated and purified by the publicly-known process for separation. The APM or AP obtained was determined with an amino-acid analyzer.

The invention now being generally described, the same will be better understood by reference to certain specific examples which are included herein for purposes of illustration only and are not intended to be limiting of the invention or any embodiment thereof.

EXAMPLE 1

Into a 500 ml-flask was introduced 50 ml of a medium (pH 7.0) containing 2.0 g/dl of glucose, 0.5 g/dl of $(NH_4)_2SO_4$, 0.1 g/dl of $KH_2PO_4$, 0.1 g/dl of $K_2HPO_4$, 0.05 g/dl of $MgSO_4.7H_2O$, 1 mg/dl of $FeSO_4.7H_2O$, 1 mg/dl of $MnSO_4.4H_2O$, 1.0 g/dl of yeast extract, 0.5 g/dl of malt extract, and 4.0 g/dl of calcium carbonate, which was sterilized at 120° C. for 15 minutes.

Each one of the thus prepared media was inoculated, using a platinum loop, with each of the microorganisms of Table 2, incubated in a bouillon-agar medium at 30° C. for 24 hours, and cultured at 30° C. for an additional 20 hours. The cells were harvested from this culture solution by centrifugation, washed once with the same amount of physiological saline as that of the culture solution and collected.

These cells of the microorganisms were added to Reaction Solution A shown in Table 1 to equal 5 g/dl (final conditions, pH 5.4, 5 ml), and allowed to react at 37° C. for 16 hours. The resulting APM was determined with an amino-acid analyzer to give the results in Table 2.

TABLE 1

| Reaction Solution A | |
| --- | --- |
| L-aspartic acid | 10 g/dl |
| L-phenylalanine methyl ester hydrochloride | 20 g/dl |

The above substrates are included in 0.1 M phosphoric acid buffer (final pH 5.4).

TABLE 2

| Microorganisms | | Reaction solution APM formed (mg/dl) |
| --- | --- | --- |
| Corynebacterium sp. | ATCC 21251 | 673 |
| Corynebacterium xerosis | ATCC 373 | 252 |
| Candida intermedia | FERM-BP | 321 |
| Cryptococcus neoformans | IFO 4289 | 142 |
| Escherichia coli | FERM-BP 477 | 915 |
| Flavobacterium sewanense | FERM-BP 476 | 820 |
| Geotrichum candidum | IFO 4599 | 156 |
| Micrococcus luteus | ATCC 4698 | 721 |
| Pachysolen tannophilus | IFO 1007 | 121 |
| Trichosporon capitatum | IFO 1197 | 127 |
| Xanthomonas campestris | FERM-BP | 328 |
| Kluyveromyces thermotolerans | IFO 0662 | 116 |
| Endomyces ovetencis | IFO 1201 | 364 |
| Saccharomyces cerevisiae | IFO 2003 | 97 |
| Arthrobacter citreus | ATCC 11624 | 910 |
| Cellulomonas flavigena | ATCC 8183 | 620 |
| Brevibacterium linens | ATCC 8377 | 820 |

EXAMPLE 2

Into 100 ml of Reaction Solution A was introduced 5 g of Flavobacterium sewanense FERM-BP 476 grown and washed in a manner similar to Example 1, and the reaction was carried out at 37° C. for 24 hours.

The resulting reaction solution was spotted on a TLC plate for development in the form of a belt, and developed with a solvent system consisting of n-butanol:acetic acid:water=2.1:1. Part of the product APM was taken out and extracted with distilled water. Then, the resulting reaction product was crystallized to obtain 560 mg of crystals. The obtained crystals were characterized as to optical rotation, melting point, and specific rotatory power, and the product obtained from Reaction Solution A was identical to an authentic APM specimen.

EXAMPLE 3

Into the culture solution of Escherichia coli FERM-BP 477 grown at 30° C. for 12 hours in the same medium used in Example 1 was poured under sterile conditions 10 ml of aqueous solution (adjusted to pH 5.4) containing 5 g/dl of L-aspartic acid and 10 g/dl of PM, and the cultivation was continued for 10 hours after the solution was adjusted under sterile conditions to pH 5.4.

It was maintained at a pH of 5.4 by adjustments at intervals of 2 hours during incubation.

The resulting product in this culture solution was verified with an amino-acid analyzer and 320 mg/dl of APM was obtained.

EXAMPLE 4

Into a 500 ml-flask was introduced 50 ml of a medium (pH 7.0) containing 2.0 g/dl of glucose, 0.5 g/dl of $(NH_4)_2SO_4$, 0.1 g/dl of $KH_2PO_4$, 0.1 g/dl of $K_2HPO_4$, 0.05 g/dl of $MgSO_4.7H_2O$, 1 mg/dl of $FeSO_4.7H_2O$, 1 mg/dl of $MnSO_4.4H_2O$, 1.0 g/dl of yeast extract, 0.5 g/dl of malt extract, and 4.0 g/dl of calcium carbonate, which was sterilized at 120° C. for 15 minutes.

Each one of the thus prepared media was inoculated, using a platinum loop, with each of the microorganisms of Table 4, incubated in a bouillon-agar medium at 30° C. for 24 hours, and cultured at 30° C. for an additional 20 hours. The cells were harvested from this culture solution by centrifugation, washed once with the same amount of physiological saline as that of the culture solution and collected.

These cells of the microorganisms were added to Reaction Solution B shown in Table 3 to equal 5 g/dl (final conditions, pH 5.4, 5 ml), and allowed to react at 37° C. for 16 hours. The resulting AP was determined with an amino acid analyzer to give the results in Table 4.

TABLE 3

| Reaction Solution B | |
| --- | --- |
| L-aspartic acid | 10 g/dl |
| L-phenylalanine | 15 g/dl |

The above substrates are included in 0.1 M phosphoric acid buffer (final pH 5.4).

TABLE 4

| Microorganisms | | Reaction solution AP formed (mg/dl) |
| --- | --- | --- |
| Corynebacterium sp. | ATCC 21251 | 391 |
| Corynebacterium xerosis | ATCC 373 | 103 |
| Candida intermedia | FERM-BP | 270 |
| Cryptococcus neoformans | IFO 4289 | 101 |
| Escherichia coli | FERM-BP 477 | 371 |
| Flavobacterium sewanense | FERM-BP 476 | 435 |
| Geotrichum candidum | IFO 4599 | 103 |
| Micrococcus luteus | ATCC 4698 | 291 |
| Pachysolen tannophilus | IFO 1007 | 93 |
| Trichosporon capitatum | IFO 1197 | 101 |
| Torulopsis inconspicua | IFO 0621 | 27 |
| Rhodotorula lactosa | IFO 1424 | 29 |
| Xanthomonas campestris | FERM-BP | 108 |
| Kluyveromyces thermotolerans | IFO 0662 | 54 |
| Endomyces ovetencis | IFO 1201 | 121 |
| Saccharcmyces cerevisiae | IFO 2003 | 63 |
| Arthrobacter citreus | ATCC 11624 | 380 |
| Cellulomonas flavigena | ATCC 8183 | 280 |
| Brevibacterium linens | ATCC 8377 | 340 |

EXAMPLE 5

Into 100 ml of Reaction Solution B was introduced 5 g of Flavobacterium sewanense FERM-BP 476 grown and washed in a manner similar to Example 4, and the reaction was carried out at 37° C. for 24 hours.

The resulting reaction solution was spotted on a TLC plate for development in the form of a belt and developed with a solvent system consisting of n-butanol:acetic acid:water=2:1:1. Part of the produced AP was taken out and extracted with distilled water. Then the resulting reaction product was crystallized to obtain 250 mg of crystals. The obtained crystals were characterized as to optical rotation, melting point, and specific rotatory power, and the product was identical to an authentic AP specimen.

EXAMPLE 6

Into the culture solution of Escherichia coli FERM-BP 477 grown at 30° C. for 12 hours in the same medium as used in Example 4 was poured under sterile conditions 10 ml of aqueous solution (adjusted to pH 5.4) containing 5 g/dl of L-aspartic acid and 7 g/dl of L-phenylalanine, and the cultivation was further continued for 10 hours after the solution was adjusted under sterile conditions to pH 5.4. It was maintained at a pH of 5.4 by adjustments at intervals of 2 hours during incubation.

The resulting product in this culture solution was verified with an amino-acid analyzer and 180 mg/dl of AP was obtained.

The invention now being fully described, it will be apparent to one of ordinary skill in the art that many changes and modifications can be made thereto without departing from the spirit or scope of the invention as set forth herein.

What is claimed as new and desired to be secured by Letters Patent of the United States is:

1. A process for the production of a sweetening agent, which comprises:

contacting in an aqueous medium L-aspartic acid and L-phenylalanine methyl ester with at least one *E. coli* FERM-BP477 microorganisms or a protein-containing material isolated from said microorganism, said microorganism or protein-containing material isolated therefrom containing one or more enzymes capable of forming L-aspartyl-L-phenylalanine methyl ester by the condensation of L-aspartic acid and L-phenylalanine methyl ester; and isolating said L-aspartyl-L-phenylalanine methyl ester formed in said aqueous medium.

2. The process of claim 1, wherein the microorganism is cultured under aerobic conditions at pH 4–8 and at a temperature of 25° C.–40° C. for a time period in the range of 1 to 10 days.

3. A process for the production of a dipeptide, which comprises:

contacting in an aqueous medium L-aspartic acid and L-phenylalanine with at least one *E. coli* FERM-BP 477 microorganism or protein-containing material isolated from said microorganism, said microorganism or protein-containing material isolated therefrom containing one or more enzymes capable of forming L-aspartyl-L-phenylalanine by the condensation of L-aspartic acid and L-phenylalanine; and isolating said L-aspartyl-L-phenylalanine from said aqueous medium.

4. The process of claim 3 wherein the microorganism is cultured under aerobic conditions at pH 4–8 and at a temperature of 25° C.–40° C. for a time period in the range of 1–10 days.

* * * * *